United States Patent [19]
Fankhauser et al.

[11] Patent Number: 6,162,447
[45] Date of Patent: Dec. 19, 2000

[54] MICROSTRUCTURED COMPOSITIONS

[75] Inventors: Peter Fankhauser, Ettingen; Rainer Hans Traber, Reinach, both of Switzerland; Dietmar Hüglin, Eimeldingen, Germany; Thomas Maier, Schliengen, Germany; Helmut Luther, Grenzach-Wyhlen, Germany; Albert Stehlin, Rosenau, France

[73] Assignee: Ciba Specialty Chemicals Corporation, Tarrytown, N.Y.

[21] Appl. No.: 09/071,644

[22] Filed: May 1, 1998

[30] Foreign Application Priority Data

May 29, 1907 [GB] United Kingdom ............... 9708909
Jul. 4, 1997 [GB] United Kingdom ............... 9714103

[51] Int. Cl.$^7$ ............... A61K 6/00; A61K 31/74; A61K 31/70; A01N 43/04; C07H 1/00
[52] U.S. Cl. ............... 424/401; 514/23; 514/54; 514/937; 514/938; 536/123.1; 536/123.12
[58] Field of Search ............... 424/401, 78.03; 514/23, 937, 54, 938; 536/123.1, 123.12

[56] References Cited

U.S. PATENT DOCUMENTS

| | | | |
|---|---|---|---|
| 3,659,025 | 4/1972 | Halleck et al. | 424/361 |
| 5,158,772 | 10/1992 | Davis | 424/401 |
| 5,814,341 | 9/1998 | Fankhauser et al. | 424/493 |

FOREIGN PATENT DOCUMENTS

| | | |
|---|---|---|
| 2050825 | 1/1981 | United Kingdom . |
| 2286530 | 8/1995 | United Kingdom . |
| 9504107 | 2/1995 | WIPO . |

OTHER PUBLICATIONS

Derwent Abst. 91–256625.
Derwent Abst. 97–029424/199703.
Derwent Abst. 92–126229/199216.

*Primary Examiner*—Thomas K Page
*Assistant Examiner*—Todd D Ware
*Attorney, Agent, or Firm*—Kevin T. Mansfield

[57] ABSTRACT

The present invention provides a microstructured cosmetic composition comprising:

A) a cosmetically acceptable oil phase which is dispersed in;

B) an aqueous phase comprising 0.05 to 3.0, preferably 0.2 to 1.0% by weight, based on the weight of the total composition, of a β-1,3-glucan having a mean molecular weight within the range of from $1 \times 10^6$ to $12 \times 10^6$, preferably from $2 \times 10^6$ to $10 \times 10^6$;

the oil phase A) in the microstructured cosmetic composition having a mean particle size within the range of from 0.05 to 1000 microns.

27 Claims, No Drawings

MICROSTRUCTURED COMPOSITIONS

The present invention relates to microstructured compositions and, in particular to a microstructured cosmetic composition comprising one or more cosmetically acceptable ingredients and a β-1,3-glucan.

In GB-A-2 050 825 there is described a skin cosmetic composition of the oil-in-water type, comprising an emulsifying agent, an oil and water, the emulsifying agent being composed of a) at least one specified glycyrrhizic compound and b) at least one water-soluble polysaccharide selected from pectin, karaya gum, locust bean gum and xanthan gum.

The polysaccharides used in GB-A-2 050 825 have certain disadvantages, namely that they contain acidic groups, rendering them sensitive to salt formation and/or variations in pH, as well as a lack of stability over an adequate temperature range.

In JP030167109 there is described a cosmetic material containing a β-1,3-glucan having a mean molecular weight greater than $10 \times 10^6$. β-1,3-glucans having a mean molecular weight greater than $10 \times 10^6$, however, are of poor aspect, and their molecular weight cannot be determined using the conventional light scattering method.

It has now been found that the use of a β-1,3-glucan having a mean molecular weight of $10 \times 10^6$ to $12 \times 10^6$ enables the formulation of microstructured cosmetic products having an excellent aspect combined with outstanding storage stability, without the need for the presence of a classical surfactant-type of emulsifier.

Accordingly, the present invention provides, as a first aspect, a microstructured cosmetic composition comprising:

A) a cosmetically acceptable oil phase which is dispersed in;

B) an aqueous phase comprising 0.05 to 3.0, preferably 0.2 to 1.0% by weight, based on the weight of the total composition, of a β-1,3-glucan having a mean molecular weight within the range of from $1 \times 10^6$ to $12 \times 10^6$, preferably from $2 \times 10^6$ to $10 \times 10^6$;

the oil phase A) in the microstructured cosmetic composition having a mean particle size within the range of from 0.05 to 1000 microns, preferably from 1 to 200 microns.

The β-1,3-glucan having a mean molecular weight within the range of from $1 \times 10^6$ to $12 \times 10^6$, component B) of the microstructured cosmetic composition according to the present invention, is described in more detail, together with its production, in GB-A-2 286 530.

Due to the molecular structure of the said β-1,3-glucan, the cosmetic composition according to the present invention forms a microstructured liquid which exhibits special rheological properties. These properties allow very easy spreading of the composition and impart good storage stability to the composition, with out separation of the respective oil and water phases.

The cosmetic composition may constitute, e.g., a shampoo and/or hair conditioner composition, in which the glucan component B), in addition to providing the microstructure, may also perform one or more of the following functions:

i) effect an improvement in the compatibility of hair treated with the shampoo/conditioner;

ii) effect an improvement in the dispersion of other components in the shampoo/conditioner;

iii) act as a smoothing agent for hair treated with the shampoo/conditioner;

iv) effect an improvement in the level of fixing of such additives as dyes or UV absorbers in the shampoo/conditioner; and v) effect improved combability of the hair treated with the shampoo/conditioner.

The cosmetic composition according to the present invention may also constitute a skin care composition, e.g., a lotion or cream in which the glucan may perform one or more of the following functions:

i) effect a lubricating function, thereby facilitating the spreading of the composition on the skin;

ii) effect a moisturising function;

iii) act as a film-forming agent, thereby providing a protective film on the skin, which film, while almost undetectable, provides the skin with a silky feel;

iv) effect a smoothing of the skin by reducing the scaling of the outermost layer of stratum corneum;

v) effect an anti-inflammatory effect on the skin; and vi) effect an improvement in the dispersion of other components of the skin care composition.

The cosmetically acceptable oil phase A) preferably comprises 5 to 50% of the total weight of the composition.

The oil phase may comprise any oil, or mixture thereof, which is known to be suitable for use in cosmetic compositions together one or more further oil-soluble conventional cosmetic ingredients such as colourants, UV absorbers, fragrances and further cosmetic active ingredients.

Examples of such oils include aliphatic hydrocarbons such as liquid paraffin, squalane, vaseline and ceresin; vegetable oils such as olive oil, jojoba oil, Scotch pine oil, tea tree oil, nigella, almond oil, sesame oil, avocado oil, castor oil, cacao butter and palm oil; animal oils such emu oil, shark liver oil, cod liver oil, whale oil, beef tallow and butter fat; waxes including bees wax, carnauba wax, spermaceti and lanolin; fatty acids such as lauric acid, myristic acid, , palmitic acid, stearic acid, oleic acid and behenic acid; aliphatic alcohols such as lauryl alcohol, stearyl alcohol, cetyl alcohol and oleyl alcohol; and aliphatic esters such as isopropyl-, isocetyl- or octadecyl myristate, butyl stearate, hexyl laurate, diisopropyl adipate or diisopropyl sebacate.

The cosmetic composition according to the present invention may constitute an anti-inflammatory skin care preparation, especially an after-sun skin care preparation.

The cosmetic composition according to the present invention may also constitute an oral care preparation, e.g., a dental gel, a denture fixation aid or a tooth paste; a mucosal lubricant formulation such as a vaginal cream or gel; or an ophthalmological preparation such as eye drops; in which the glucan component B) may perform one or more of the following functions:

i) effect lubrication of dry mucosae;

ii) effect thickening of liquid preparations;

iii) effect retention of active ingredients by formation of films on mucosal surfaces; and iv) effect an improvement in the dispersion of other components in the composition.

When the β-1,3-glucan is used in an ophthalmological preparation, it may be used together with other components such as:

a) ophthalmological active ingredients e.g. Gentamicin sulphate, Lomefloxacin hydrochloride, Chloramphenicol, Sodium Diclofenac, Potassium Diclofenac, Dexamethason di-sodium phosphate, Naphazolin nitrate, Tetryzolin hydrochloride, Antazolin hydrochloride, Antazolin sulphate, Pilocarpin chloride, Vitamin A-palmitate and zinc sulphate;

b) ophthalmological buffers such as boric acid, borax, acetic acid, sodium acetate, phosphoric acid, sodium dihydrogen phosphate, disodium hydrogen phosphate, sodium phosphate, Trometamol, citric acid and sodium citrate;

c) ophthalmological preservatives such as benzyl alkylammonium chloride, benzoxonium chloride, chlorhexidine digluconate, chlorobutanol, phenylethyl alcohol and Thiomersal;

d) solvents such as ethanol, glycerol, polyethylene glycol and water;

e) isotonising agents such as sodium chloride, mannitol and sorbitol, f) chelate formers such as disodium EDTA;

g) antioxidants such as α-tocopherol acetate, ascorbic acid, N-acetyl-cystine, sodium bisulphite, sodium thiosulphate and propyl gallate; and h) viscosity-increasing compounds such as methylhydroxypropyl cellulose, Carbopol 934P, Carbopol 940, Carbopol 980 and Poloxamer F127.

The cosmetic composition of the invention may also comprise further non-surfactant components which are known to perform a useful function in a cosmetic composition. Examples of such further components include, e.g., emollients, skin moisturisers, UV absorbers such as:

1. p-aminobenzoic acid derivatives, typically 2-ethylhexyl 4-dimethylaminobenzoate;
2. salicylic acid derivatives, typically 2-ethylhexyl salicylate;
3. benzophenone derivatives, typically 2-hydroxy-4-methoxybenzophenone and its 5-sulfonic acid derivative;
4. dibenzoylmethane derivatives, typically 1-(4-tert-butylphenyl)-3-(4-methoxyphenyl)-propane-1,3-dione;
5. diphenylacrylates, typically 2-ethylhexyl-2-cyano-3,3-diphenylacrylate and 3-(benzofuranyl)-2-cyanoacrylate;
6. 3-imidazol-4-yl-acrylic acid and 3-imidazol-4-yl-acrylate;
7. benzofuran derivatives, preferably 2-(p-aminophenyl) benzofuran derivatives, disclosed in EP-A-582,189, U.S. Pat. No. 5,338,539, U.S. Pat. No. 5,518,713 and in EP-A-613,893;
8. polymeric UV absorbers, such as the benzylidenemalonate derivatives described, inter alia, in EPA-709,080;
9. cinnamic acid derivatives, typically the 2-ethylhexyl 4methoxycinnamate or isoamylate or cinnamic acid derivatives disclosed, inter alia, in U.S. Pat. No. 5,601,811 and WO 97/00851;
10. camphor derivatives, typically 3-(4'-methyl) benzylidenebornan-2-one, 3-benzylidene-bornan-2-one, N-[2(and 4)-2-oxyborn-3-ylidenemethyl)benzyl] acrylamide polymer, 3-(4'-trimethylammonium) benzylidenebornan-2-one methyl sulfate, 3,3'-(1,4-phenylenedime-thine)-bis(7,7-dimethyl-2-oxo-bicyclo-[2.2.1]heptane-1-methansulfonic acid) and the salts thereof, 3-(4'-sulfo)benzylidenebornan-2-one and the salts thereof;
11. trianilino-s-triazine derivatives, typically 2,4,6-trianiline-(p-carbo-2'-ethyl-1'-oxi)-1,3,5-triazines as well as the UV absorbers disclosed in U.S. Pat. No. 5,332,568, EP-A-517,104, EP-A-507,691, WO 93/17002 and EP-A-570,838;
12. 2-hydroxyphenylbenzotriazole derivatives;
13. 2-phenylbenzimidazole-5-sulfonic acid and the salts thereof; 14. menthyl-o-aminobenzoate; 15. $TiO_2$ (coated differently), ZnO and mica; additional thickening agents such as xanthan, moisture-retention agents such as glycerine, film formers, preservatives, antimicrobial agents, perfumes, colourants and solvents such as alcohols, cyclodimethicones and ketones.

Due to their microstructure, the cosmetic compositions of the invention may also contain microcapsules, capsules or pellets of larger size (e.g. up to several mms., preferably from 50 microns to 5 mm), for the purpose, e.g., of releasing additional ingredients or for decorative purposes, without exhibiting sedimentation problems.

The β-1,3-glucan component of the cosmetic composition of the present invention contains in its structure β-1,3-bonded glucopyranose as the main chain and β-1,6-bonded glucopyranose as side chains and has the structural formula:

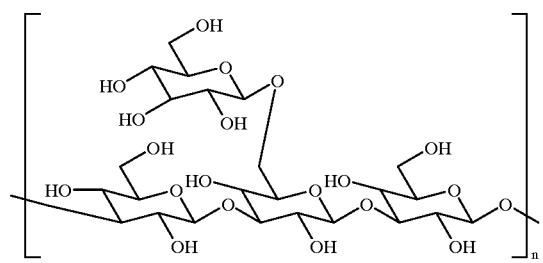

in which n is a number which provides the β-1,3-glucan component with a mean molecular weight (MW) of $1 \times 10^6$ to $12 \times 10^6$, preferably $2 \times 10^6$ to $10 \times 10^6$, determined from the readil measured Staudinger Index η using the following Mark-Houwink equation: $MW=[\eta/4.45.10^{-7}]^{1/1.49}$.

Preferably, a 0.3 g/l aqueous solution of the β-1,3-glucan has a glucose content below 0.1 g/l and a viscosity of 50 to 190 mPa.s, measured at a shear rate of 0.3 $s^{-1}$ at 40° C.

A preferred β-1,3-glucan component of the cosmetic composition of the present invention is a β-1,3-scleroglucan having a three-dimensional crosslinked triple helix structure and having a mean molecular weight of $1 \times 10^6$ to $12 \times 10^6$, preferably $2 \times 10^6$ to $10 \times 10^6$.

This β-1,3-scleroglucan is produced using the plant-pathogenic fungi imperfecti Sclerotium rolfsii ATCC 15205. This process is characterized in that microorganisms, in the form of the plant-pathogenic fungi imperfecti Sclerotium rolfsii ATCC 15205 are cultivated in a culture medium under microaerobic conditions.

The basic cultivation medium used may be that described in U.S. Pat. No. 3,301,848 comprising a carbon source; a nitrogen source such as an ammonium salt or, preferably, sodium nitrate; a phosphate source such as dipotassiumhydrogen phosphate trihydrate; potassium chloride; magnesium sulfate heptahydrate; ferric sulfate heptahydrate; and yeast extract. The use of dipotassiumhydrogen phosphate trihydrate as phosphate source has the advantage that it acidifies the medium and therefore obviates the need for a separate acid to adjust the medium to a pH value of about 2.

In a preferred embodiment, glucose is used as the carbon source. The glucose is converted to β-1,3-scleroglucan, biomass, $CO_2$ and oxalic acid, which is the only detectable by-product. To this basic medium are preferably added citric acid hydrate, preferably in an amount ranging from 0.2 to 1.5 g/l; thiamine or a mineral acid salt thereof, preferably in an amount ranging from 0.3 to 30 mg/l; and a zinc salt such as zinc sulfate, preferably in an amount ranging from 0.3 to 30 mg/l. While the yeast extract per se is a source of both thiamine and zinc, yeast extract does not provide these ingredients in sufficient amounts to provide optimum yields of the desired β-1,3-scleroglucan product.

It has been found that, by reducing the amount of oxygen used, the amounts of $CO_2$ and biomass formed are reduced, with consequent increased formation of the desired β-1,3-scleroglucan. Accordingly, it is preferred to operate the process using a specific oxygen uptake rate (oxygen uptake rate based on the biomass) within the range of from 0.01 to 0.08 $h^{-1}$. Preferably, a nitrogen-limited cultivation preculture (inoculum) is used. Surprisingly, it has been found that the use of a nitrogen-limited preculture, as inoculum in the cultivation, leads to an improved product-to-biomass ratio. It is preferred to operate the process using amounts of nitrogen source in the cultivation medium ranging from 0.2 to 0.8 g N/l. Preferably, the cultivation process is effected with agitation, at 15 to 40° C.; the culture solution is then separated from the mass of cells; and the β-1,3-scleroglucan product so obtained is isolated in conventional manner. As the reactor size increases, the importance of an adequate mixing of the highly-viscous medium rises. A reduced level of mixing leads to a strong decrease in the rate of growth and polysaccharide formation during the cultivation. In order to achieve adequate mixing in large reactors, it is standard practice to operate with high stirrer speeds. In the case of scleroglucan production, however, high mean shear rates and maximum stirrer speeds in the reactor degrade the polysaccharide. It has now been found that equally good mixing can be attained, in a comparable time, using very high gasification rates. In this way, the gasification mainly takes over the task of effecting axial mixing of the medium. High gasification rates also ensure a rotation of the highly-viscous reactor volume up to the end of the cultivation. Such a less severe mixing enables the production of a higher molecular product. The stirring device effects the necessary shearing off of the polysaccharide from the cell surfaces. The mean shear rates in the reactor preferably range from 18 to 25 $s^{-1}$ and the maximum stirrer speed preferably ranges from 0.7 to 1.0 m/s. Moreover, the high proportion of gas in the liquid leads to a lowering of the density of the total system and thus to a reduction of the viscosity.

The cosmetic composition of the invention may be prepared by any conventional blending technique such as conventional stirring, shaking or tumbling. A preferred technique is high-speed stirring, e.g. using a rotor-stator dispersing device, or using high pressure homogenisation, e.g. in a microfluidizer. Preferably, an aqueous solution containing from 0.05 to 5% by weight of β-1,3-glucan and a cosmetically acceptable oil may be subjected to a conventional blending technique in which the oil phase A) may be heated to a temperature above the melting point of its components. Alternatively, the aqueous phase B) and the oil phase A) may be heated, under pressure, to a temperature above the boiling point of water, e.g. to a temperature of up to 200° C.

The present invention is further illustrated by the following Examples. Parts and percentages shown therein are by weight unless otherwise stated.

EXAMPLE 1

900 g of a 1.0% aqueous solution of β-glucan are placed in a double-jacketed reactor fitted with a thermostat and are heated to 60° C., with gentle stirring, using a glass anchor stirrer. The speed of the stirrer is then increased to 800 rpm and 100 g of jojoba oil are poured into the reactor. The mixture is further blended for 30 minutes at the same temperature and stirring rate.

The gel so obtained is protected against microbial attack by the addition of 0.4% by weight of 2-phenoxyethanol. The resulting gel contains an oil phase which has a mean particle size within the range of from 5 to 100 microns and shows no phase separation after being stored in a heating cabinet at 40° C. for 20 days.

EXAMPLE 2

100 g of emu oil are placed in a double-jacketed reactor fitted with a thermostat and are heated to 60° C., with gentle stirring using a glass anchor stirrer. Then 900 g of a 1.0% aqueous solution of β-glucan, which has previously been heated to 60° C. in a warming cabinet, are poured into the reactor. During the course of the addition of the β-glucan solution, the speed of the stirrer is then increased to 800 rpm. The mixture is further blended for 30 minutes at the same temperature and stirring rate.

The gel so obtained is protected against microbial attack by the addition of 0.4% by weight of 2-phenoxyethanol. The resulting gel contains an oil phase which has a mean particle size within the range of from 10 to 200 microns and shows no phase separation after being stored in a heating cabinet at 40° C. for 20 days.

EXAMPLE 3

A) 800 g of a 1.0% aqueous solution of β-glucan are placed in a double-jacketed reactor fitted with a thermostat and are heated to 60° C., with gentle stirring using a glass anchor stirrer.

B) In a separate operation, 100 g of Scotch pine oil and 100 g of a 1.0% aqueous solution of β-glucan are blended in a beaker using a rotor-stator dispersing device and using a coarse stator insert, for 1 minute at 8000 rpm. This mixture is then added to the solution prepared in step A) and the speed of the stirrer used in step A) is increased to 800 rpm and blending is conducted for 30 minutes at 60° C.

The gel so obtained is protected against microbial attack by the addition of 0.4% by weight of 2-phenoxyethanol. The resulting gel contains an oil phase which has a mean particle size within the range of from 5 to 100 microns and shows no phase separation after being stored in a heating cabinet at 40° C. for 20 days.

EXAMPLE 4

850 g of a 1.0% aqueous solution of β-glucan are placed in a double-jacketed reactor fitted with a thermostat and are heated to 60° C., with gentle stirring using a glass anchor stirrer. The speed of the stirrer is then increased to 800 rpm and 100 g of jojoba oil are poured into the reactor. The mixture is further blended for 10 minutes at the same temperature and stirring rate. 20 g of titanium dioxide powder are then sprinkled into the mixture and the whole mixture is stirred for 30 minutes at 60° C. and at 800 rpm.

The gel so obtained is protected against microbial attack by the addition of 0.4% by weight of 2-phenoxyethanol. The resulting gel shows no phase separation after being stored in a heating cabinet at 40° C. for 20 days.

EXAMPLES 5–10

Surfactant-free Formulations Comprising β-glucan

EXAMPLE 5

15 g of glycerine are added to 35 g of a 1% β-glucan solution at ca. 50° C. and stirred within 15 minutes at this temperature. The mixture is cooled down to room temperature. A high-viscous solution is formed after ca. 2 hours.

Instead of glycerine di- tri and polyglycerines, sorbitol, glucose, low molecular polyethylene glycol and polyhydroxy compounds as sugar may be used.

EXAMPLE 6

15 g of 1.2-propyleneglycol are added to 35 g of a 1% β-glucan solution at ca. 50° C. and stirred within 15 minutes at this temperature. The solution is cooled down to room temperature. A clear solid gel is formed after ca. 2 hours.

EXAMPLE 7

5 g of PEG 600 and 10 g of water are added to 35 g of a 1% β-glucan solution at ca. 50° C. and stirred within 15 minutes at this temperature. The solution is cooled down to room temperature. A clear solid gel is formed after ca. 24 hours.

EXAMPLE 8

10 g of 2-methyl-2.4-pentandiol and 5 g of water are added to 35 g of a 1% β-glucan solution at ca. 50° C. and stirred within 15 minutes at this temperature. The solution is cooled down to room temperature. A clear solid gel is formed after ca. 24 hours.

EXAMPLE 9

15 g of 1.2-pentanediol is added to 35 g of a 1% β-glucan solution at ca. 50° C. and stirred within 15 minutes at this temperature. The solution is cooled down to room temperature. A clear solid gel is formed after ca. 2 hours.

EXAMPLE 10

10 g of 1.2-pentandiol and 5 g of water are added to 35 g of a 1% β-glucan solution at ca. 50° C. and stirred within 15 minutes at this temperature. The solution is cooled down to room temperature. An opaque viscous solution is formed after ca. 24 hours (no gel formation).

EXAMPLES 11–17

Incorporation of a UV Absorber into a Gel

A sun-protecting gel is prepared as follows:

The oil phase (A) and the water-phase (B) are heated separately to 60° C. Then phase (A) is stirred into phase (B) at 1200 rpm and cooled down with stirring afterwards. A solid gel of fine particles is formed.

The sun protection factors are determined according to the method of Diffey and Robson, J. Soc. Cosmet. Chem. 40, 127–133 (1989) using an SPF analyser (Optometrix, SPF 290). A thickness layer of 2 $\mu l/cm^2$ was applied on a transpore-film of 3M.

EXAMPLE 11

| Phase A | $C_{12-15}$alkylbenzoate | 25% |
| | compound of the formula (101) | 2.0% |
| Phase B | water | 3.0% |
| | PEG 600 | 10.0% |
| | β-glucan (1%) | 60.0% |

The formulation is a viscous gel with a SPF factor of 4.6.

EXAMPLE 12

| Phase A | $C_{12-15}$alkylbenzoate | 25% |
| | compound of the formula (101) | 2.0% |
| | 4-methylbenzylidene camphor | 3.0 |
| Phase B | PEG 600 | 10.0% |
| | β-glucan (1%) | 60.0% |

The formulation is a beige-coloured viscous gel with a SPF factor of 5.0.

EXAMPLE 13

| Phase A | diisopropyladipate | 10% |
| | octylmethoxycinnamate | 3.0% |
| Phase B | water | 7.0% |
| | 1.2-propyleneglycol | 30.0% |
| | β-glucan (1%) | 50.0% |

The formulation is a white high-viscous gel with a SPF factor of 3.6.

EXAMPLE 14

| Phase A | diisopropyladipate | 10% |
| --- | --- | --- |
|  | octylmethoxycinnamate | 3.0% |
| Phase B | water | 3.8% |
|  | 1.2-propyleneglycol | 30.0% |
|  | β-glucan (1%) | 45.0% |
|  | phenylbenzimidazole sulfonic acid | 5.0% |
|  | triethanolamine | 3.2% |

The formulation is an opaque viscous gel with a SPF factor of 4.4.

EXAMPLE 15

| Phase A | diisopropyladipate | 10% |
| --- | --- | --- |
| Phase B | 1,2-propyleneglykol | 30.0% |
|  | β-glucan (1%) | 60.0% |
|  | Tioveil AQ-G (40%) (TiO$_2$) | 10.0% |

The formulation is a white viscous gel with a SPF factor of 2.7.

EXAMPLE 16

| Phase A | diisopropyladipate | 10% |
| --- | --- | --- |
|  | octylmethoxycinnamate | 3.0% |
| Phase B | water | 7.0% |
|  | PEG 600 | 10.0% |
|  | β-glucan (1%) | 60.0% |
|  | UV-absorber dispersion comprising | 10.0% |

50.0% 2.2'-mehtylen-bis-(6-(2H-benztriazol-2-yl)-4-(1,1,3,3-tetramethylbutyl)-phenol 15.0% C$_{8-16}$-fattyalcoholglycoside 34.4% water 0.2% Xanthane gum 0.4% 1.2-propyleneglycol

EXAMPLE 17

| Phase A | diisopropyladipate | 10% |
| --- | --- | --- |
| Phase B | water | 10.0% |
|  | PEG 600 | 10.0% |
|  | β-glucan (1%) | 60.0% |
|  | UV-absorber dispersion comprising | 10.0% |

50.0% 2.2'-mehtylen-bis-(6-(2H-benztriazol-2-yl)-4-(1,1,3,3-tetramethylbutyl)-phenol 15.0% C$_{8-16}$-fatty alcohol glyco side 34.4% water 0.2% Xanthane gum 0.4% 1.2-propyleneglycol Application Examples:

EXAMPLE 18
Preparation of a Moisturizing Skin Cream

| Phases | INCI Name | % b.w. |
| --- | --- | --- |
| A | passionflower oil | 4 |
|  | jojoba oil | 6 |
| B | β-glucan (1% in water) | 80 |
|  | aqua | ad. 100 |
| C | perfume, preservative | q.s. |

Procedure: Phases A and B are heated separately to 60–70° C. Phase A is then added slowly to phase B while homogenizing. Homogenization is continued for another minute. While stirring the mixture is cooled down to 40° C. and phase C is added. Homogenization is continued for 1 minute and cooled down to 25° C. while stirring.

EXAMPLE 19
Preparation of a Hair conditioner

| Phases | INCI Name | % b.w. |
| --- | --- | --- |
| A | jojoba Oil | 6 |
|  | cyclomethicone | 0.25 |
| B | β-glucan (1% in water) | 80 |
|  | aqua | ad. 100 |
|  | perfume, preservative | q.s. |

Procedure: Phases A and B are heated separately to 60–70° C. Phase A is then added slowly to phase B while homogenizing for another ½ minute. While stirring the mixture is cooled down to 40° C. and phase C is added. Homogenization is continued for 1 minute and cooled down to 25° C. while stirring.

EXAMPLE 20
Preparation of a Cream Facial Scrub

| Phases | INCI Name | % b.w. |
| --- | --- | --- |
| A | mineral oil | 5 |
|  | safflower oil | 1 |
|  | sesame oil | 2 |
| B | β-glucan (1% in water) | ad. 100 |
| C | phenoxyethanol | 0.75 |
|  | perfume | q.s |

Procedure: Phases A and B are heated separately to 60–70° C. Phase A is then added slowly to phase B while homogenizing for another minute. While stirring the mixture is cooled down to 40° C. and phase C is added. Homogenization is continued for 1 minute and cooled down to 25° C. while stirring.

EXAMPLE 21
Preparation of a After Sun Gel

| Phases | INCI Name | % b.w. |
| --- | --- | --- |
| A | jojoba Oil | 3 |
|  | evening primrose oOil | 3 |
|  | D-pPanthenol | 1 |

-continued

| Phases | INCI Name | % b.w. |
|---|---|---|
| B | β-glucan (1% in water) | 80 |
| C | tocopheryl acetate | 0.50 |
|   | perfume, preservative | q.s |

Procedure: Phases A and B are heated separately to 60–70° C. Phase A is then added slowly to phase B while homogenizing for another 2 minutes. While stirring it is cooled down to 40° C. and phase C is added. Homogenization is continued for 1 minute and cooled down to 25° C. while stirring.

EXAMPLE 22
Preparation of a Mucosal Lubricant Gel

| Phases | INCI Name | % b.w. |
|---|---|---|
| A | jojoba Oil | 5 |
| B | β-glucan (1% in water) | ad. 100 |
| C | phenoxyethanol | 0.75 |

Procedure: Phases A and B are heated separately to 60–70° C. Phase A is then added slowly to phase B while homogenizing for another minute. Phase C is added and cooled down to ambient temperature while stirring.

EXAMPLE 23
Preparation of a Dental Gel

| Phases | INCI Name | % b.w. |
|---|---|---|
| A | Sesame Oil | 3 |
|   | Pistachio Nut Oil | 3 |
| B | β-glucan (1% in water) | 80 |
|   | Sodium Saccharin | 0.2 |
|   | Sodium monofluorophosphate | 0.3 |
|   | Blue FD&C No. 1 | 0.001 |
|   | Aqua | ad. 100 |
| C | Preservative | q.s. |

Procedure: Phases A and B are heated separately to 60–70° C. Phase A is then added slowly to phase B while homogenizing for another minute. Phase C is added and cooled down to ambient temperature while stirring.

What is claimed is:

1. A microstructured cosmetic composition comprising:
   A) a cosmetically acceptable oil phase which is dispersed in;
   B) an aqueous phase comprising 0.05 to 3.0% by weight, based on the weight of the total composition, of a β-1,3-glucan having a mean molecular weight within the range of from $1 \times 10^6$ to $12 \times 10^6$;
      the oil phase A) in the microstructured cosmetic composition having a mean particle size within the range of from 0.05 to 1000 microns,
      excluding compositions comprising a surfactant.

2. A microstructured cosmetic composition according to claim 1 which contains 0.2 to 1.0% by weight, based on the weight of the total composition, of the β-1,3-glucan component B).

3. A microstructured cosmetic composition according to claim 1 in which the β-1,3-glucan component B) has a mean molecular weight within the range of from $2 \times 10^6$ to $10 \times 10^6$.

4. A microstructured cosmetic composition according to claim 1 in which oil phase A) in the microstructured cosmetic composition has a mean particle size within the range of from 1 to 200 microns.

5. A microstructured cosmetic composition according to claim 1 in which the microstructured cosmetic composition is a shampoo and/or hair conditioner composition.

6. A microstructured cosmetic composition according to claim 1 in which the microstructured cosmetic composition is a skin care composition.

7. A microstructured cosmetic composition according to claim 1 in which the cosmetically acceptable oil phase A) comprises 5 to 50% of the total weight of the composition.

8. A microstructured cosmetic composition according to claim 7 in which the cosmetically accepted oil phase A) is an aliphatic hydrocarbon; a vegetable oil; an animal oil; a wax; a fatty acid; an aliphatic alcohol; or an aliphatic ester.

9. A microstructured cosmetic composition according to claim 8 in which the aliphatic hydrocarbon is liquid paraffin, squalane, vaseline or ceresin; the vegetable oil is olive oil, jojoba oil, Scotch pine oil, tea tree oil, nigella oil, almond oil, sesame oil, avocado oil, castor oil, cacao butter or palm oil; the animal oil is emu oil, shark liver oil, cod liver oil, whale oil, beef tallow or butter fat; the wax is bees wax, carnauba wax, spermaceti or lanolin; the fatty acid is lauric acid, myristic acid, palmitic acid, stearic acid, oleic acid or behenic acid; the aliphatic alcohol is lauryl alcohol, stearyl alcohol, cetyl alcohol or oleyl alcohol; and the aliphatic ester is isopropyl-, isocetyl- or octadecyl myristate, butyl stearate, hexyl laurate, diisopropyl adipate or diisopropyl sebacate.

10. A microstructured cosmetic composition according claim 1 in which the microstructured cosmetic composition is an anti-inflammatory skin care preparation.

11. A microstructured cosmetic composition according to claim 10 in which the anti-inflammatory skin care preparation is an after-sun skin care preparation.

12. A microstructured cosmetic composition according to claim 1 in which the microstructured cosmetic composition is an oral care preparation, a mucosal lubricant formulation or an ophthalmological preparation.

13. A microstructured cosmetic composition according to claim 12 in which the oral care preparation is a dental gel, a denture fixation aid or a tooth paste; the mucosal lubricant formulation is a vaginal cream or gel; and the ophthalmological preparation is eye drops.

14. A microstructured cosmetic composition according to claim 13 in which the β-1,3-glucan is used in an ophthalmological preparation together one or more of:
   a) an ophthalmological active ingredient;
   b) an ophthalmological buffer;
   c) an ophthalmological preservative;
   d) a solvent;
   e) an isotonising agent;
   f) a chelate former;
   g) an antioxidant; and
   h) a viscosity-increasing compound.

15. A microstructured cosmetic composition according to claim 14 in which
   a) the ophthalmological active ingredient is Gentamicin sulphate, Lomefloxacin hydrochloride, Chloramphenicol, Sodium Diclofenac, Potassium Diclofenac, Dexamethason di-sodium phosphate, Naphazolin nitrate, Tetryzolin hydrochloride, Antazolin hydrochloride, Antazolin sulphate, Pilocarpin chloride, Vitamin A-palmitate or zinc sulphate;
   b) the ophthalmological buffer is boric acid, borax, acetic acid, sodium acetate, phosphoric acid, sodium dihydrogen phosphate, disodium hydrogen phosphate, sodium phosphate, Trometamol, citric acid or sodium citrate;

c) the ophthalmological preservative is benzoxonium chloride, chlorhexidine digluconate, chlorobutanol, phenylethyl alcohol or Thiomersal;

d) the solvent is ethanol, glycerol, polyethylene glycol (PEG) or water;

e) the isotonising agent is sodium chloride, mannitol or sorbitol;

f) the chelate former is disodium EDTA;

g) the antioxidant is α-tocopherol acetate, ascorbic acid, N-acetyl-cystine, sodium bisulphite, sodium thiosulphate or propyl gallate; and h) the viscosity-increasing compound is methylhydroxypropyl cellulose, carbomer 934P, carbomer 940, carbomer 980.

16. A microstructured cosmetic composition according to claim 1 in which the cosmetic composition also comprises one or more further non-surfactant components, in which the further non-surfactant component is an emollient, a skin moisturiser, a UV absorber, an additional thickening agent, a moisture-retention agent, a film former, a preservative, an antimicrobial agent, a perfume a colourant, or a mixture thereof and which are liquid, semi-solid or solid and which have a mean particle size within the range of from 0.05 micron to 1 mm.

17. A microstructured cosmetic composition according to claim 1 in which the cosmetic composition also comprises one or more components in the form of microcapsules, capsules or pellets which have a particle size of from 50 microns to 5 mm.

18. A microstructured cosmetic composition according to claim 16 in which the UV absorber is an oxanilide, a triazine or triazole, the additional thickening agent is xanthan and the moisture-retention agent is glycerine.

19. A microstructured cosmetic composition according to claim 1 in which the β-1,3-glucan component of the cosmetic composition contains in its structure β-1,3-bonded glucopyranose as the main chain and β1,6-bonded glucopyranose as side chains and has the structural formula:

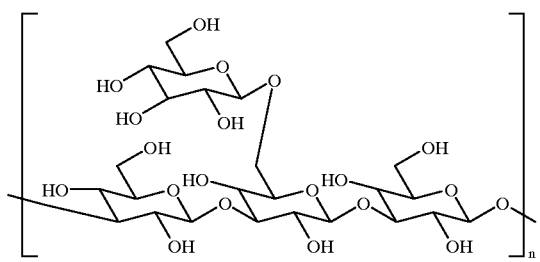

in which n is a number which provides the β-1,3-glucan component with a mean molecular weight (MW) of $1 \times 10^6$ to $12 \times 10^6$, determined from the readily measured Staudinger Index η using the following Mark-Houwink equation.

20. A microstructured cosmetic composition according to claim 19 in which a 0.3 g/l aqueous solution of the β-1,3-glucan has a glucose content below 0.1 g/l and a viscosity of 50 to 190 mPa.s, measured at a shear rate of 0.3 $s^{-1}$ at 40° C.

21. A microstructured cosmetic composition according to claim 1 in which the β-1,3-glucan component of the cosmetic composition is a β-1,3-scleroglucan having a three-dimensional crosslinked triple helix structure and having a mean molecular weight of $1 \times 10^6$ to $12 \times 10^6$.

22. A microstructured cosmetic composition according to claim 21 in which the β-1,3-scleroglucan is produced using the plant-pathogenic fungi imperfecti *Sclerotium rolfsii* ATCC 15205.

23. A microstructured cosmetic composition according to claim 22 in which the β-1,3-scleroglucan is produced by cultivating microorganisms, in the form of the plant-pathogenic fungi imperfecti *Sclerotium rolfsii* ATCC 15205 in a culture medium under microaerobic conditions.

24. A process for the production of a microstructured cosmetic composition according to claim 1 comprising subjecting the oil phase A) and the aqueous phase B) to a blending technique.

25. A process according to claim 24 in which the blending technique is a stirring, shaking or tumbling technique.

26. A process according to claim 25 in which the conventional blending technique is high speed stirring or high pressure homogenization.

27. A process according to claim 24 in which the aqueous phase B) is an aqueous solution.

* * * * *

UNITED STATES PATENT AND TRADEMARK OFFICE
CERTIFICATE OF CORRECTION

PATENT NO. : 6,162,447
DATED : December 19, 2000
INVENTOR(S) : Peter Fankhauser et al.

Page 1 of 1

It is certified that error appears in the above-identified patent and that said Letters Patent is hereby corrected as shown below:

On the title page, Section [30] should read:
--[30] Foreign Application Priority Data
    May 2, 1997 [GB] United Kingdom    9708909.8
    Jul. 4, 1997 [GB] United Kingdom    9714103.0

Signed and Sealed this

Tenth Day of July, 2001

*Attest:*

NICHOLAS P. GODICI
*Attesting Officer*    *Acting Director of the United States Patent and Trademark Office*